US006267731B1

(12) United States Patent
Kroll et al.

(10) Patent No.: US 6,267,731 B1
(45) Date of Patent: Jul. 31, 2001

(54) METHOD AND APPARATUS FOR REDUCED FEEDBACK IN IMPLANTABLE HEARING ASSISTANCE SYSTEMS

(75) Inventors: Kai Kroll, Minnetonka; Donald J. Bushek, Plymouth; Scott C. Meyerson, Moundsview; Paul J. Urbanski, Minneapolis, all of MN (US)

(73) Assignee: St. Croix Medical, Inc., Minneapolis, MN (US)

(*) Notice: Subject to any disclaimer, the term of this patent is extended or adjusted under 35 U.S.C. 154(b) by 0 days.

(21) Appl. No.: 09/327,345

(22) Filed: Jun. 5, 1999

Related U.S. Application Data

(60) Provisional application No. 60/088,162, filed on Jun. 5, 1998, provisional application No. 60/088,276, filed on Jun. 5, 1988, and provisional application No. 60/088,319, filed on Jun. 5, 1998.

(51) Int. Cl.[7] ......................................................... A61B 5/00
(52) U.S. Cl. ............................................................. 600/559
(58) Field of Search ................................ 600/559; 73/585

(56) References Cited

U.S. PATENT DOCUMENTS 5,386,475 * 1/1995 Birck et al. ........................... 600/559
6,113,531 * 9/2000 Leysieffer et al. ................... 600/559

* cited by examiner

Primary Examiner—Max Hindenburg
(74) Attorney, Agent, or Firm—Fredrikson & Byron, P.A.

(57) ABSTRACT

A method and apparatus assists a hearing impaired person by introducing and maintaining a mechanical feedback barrier between a microphone and a transducer of an implantable hearing assistance system. In this method, mechanical sound vibrations impinging on the person's body habitus are received with an electromechanical device (e.g. microphone) disposed at a body habitus sound reception site. The body habitus sound reception site can be located within the external auditory canal, or external of the external auditory canal either subdermally or external of the scalp. The mechanical sound vibrations are converted with the electromechanical device to an amplified electrical signal. Next, the amplified electrical signal is delivered to the inner ear with a transducer operatively coupled between the electromechanical device and the middle ear or the inner ear. Finally, a mechanical feedback barrier is introduced and maintained between the sound reception site and the transducer to minimize acoustic feedback therebetween. Preferably, this feedback barrier is established by removing, separating, or fixing, or combinations thereof, a portion of the hearing impaired person's ossicular chain (e.g malleus, incus, or stapes).

63 Claims, 7 Drawing Sheets

METHOD AND APPARATUS FOR REDUCED FEEDBACK IN IMPLANTABLE HEARING ASSISTANCE SYSTEMS

CROSS-REFERENCE TO RELATED APPLICATION

This application claims priority under 35 U.S.C. § 119 (e) to, and hereby incorporates by reference, U.S. Provisional Application Nos. 60/088,162; 60/088,276; and 60/088,319, all filed Jun. 5, 1998.

1. Field of the Invention

The present invention relates to implantable hearing systems for assisting hearing in hearing impaired persons.

2. Description of Related Art

Some implantable hearing assistance systems use a microphone located in or near the ear to convert acoustic sound energy into an electrical signal. The electric signal is amplified, modulated and then directly communicated by a transducer to the inner ear to stimulate the cochlea to assist hearing. Alternatively, the amplified signal is communicated to a transducer for conversion to mechanical acoustic energy for vibratory application to the stapes of the middle ear or the cochlea. The microphone can be located externally, subdermally adjacent the ear, or within the external auditory canal. The transducer is commonly connected to a portion of the middle ear, known as the ossicular chain, which includes the malleus, incus and stapes. Vibrations are emitted from the transducer into and through the ossicular chain to the cochlea of the inner ear.

The ossicular chain facilitates forward transmission of mechanical sound vibrations from the tympanic membrane of the external auditory canal to the inner ear. However, the ossicular chain also permits reverse transmission of mechanical sound energy to be transmitted from the transducer of the implantable hearing assistance system, back through the ossicular chain to the tympanic membrane, and into the external auditory canal. This retrograde sound transmission passes out of the external auditory canal and is acoustically fed back to the microphone of the system.

This acoustic feedback limits the maximum gain which the hearing assistance system can apply to the signal received by the microphone. In particular, the feedback created by reverse bone conduction through the ossicular chain has an inverse relationship with usable gain. For example, if one percent of the acoustic vibratory signal emitted by the transducer to the stapes, or other part of the ossicular chain, is fed back through the ossicular chain and into the external auditory canal to the microphone, the gain for the hearing assistance system is limited to roughly 100 or 40 dB. Due to the nature of the hearing losses and the acoustic limitations of these systems, a much higher gain is ideal. Accordingly, reduction or elimination of this feedback is desirable.

Moreover, these hearing assistance systems, which transmit acoustic sound energy onto an ossicular chain with a transducer, are inefficient and consume power rapidly. Inefficiency results from the mechanical force that must be exerted by the transducer against the ossicular chain. This inefficiency causes rapid power consumption, requiring frequent battery changes. Battery changes are, at least, inconvenient for an externally located battery, and at worst, costly and surgically- related for a battery implanted in the middle ear or subdermally.

The importance of restoring hearing to hearing impaired persons demands more optimal solutions in hearing assistance systems. Ideally, an improved hearing assistance system both minimizes power consumption as well as maximizes gain to produce a better acoustic signal for reception into the cochlea and the inner ear.

SUMMARY OF THE INVENTION

A method and apparatus of the present invention improves hearing for a hearing impaired person by introducing and maintaining a mechanical feedback barrier between a microphone and a transducer of an implantable hearing assistance system. In this method, mechanical sound vibrations impinging on the person's body habitus are received with an electromechanical device (e.g. microphone) disposed at a body habitus sound reception site. The body habitus sound reception site can be located within the external auditory canal, or external of the external auditory canal either subdermally or external of the scalp, or even subdermally along the external auditory canal.

The mechanical sound vibrations are converted with the electromechanical device to an amplified electrical signal. Next, the amplified electrical signal is delivered to the inner ear with a transducer operatively coupled between the electromechanical device and the middle ear or the inner ear.

Finally, a mechanical feedback barrier is introduced and maintained between the sound reception site and the transducer to minimize acoustic feedback therebetween. Preferably, this feedback barrier is established by removing a portion of the hearing impaired person's ossicular chain (e.g. malleus, incus, or stapes) or fixing a portion of the ossicular chain to prevent transmission of sound feedback. In other embodiments, a portion of the ossicular chain is not removed but merely separated so that the procedure can be reversed if desired at a later time.

This method and apparatus of the present invention optimizes hearing improvement by preventing unnecessary mechanical feedback that can occur through the ossicular chain and the external auditory canal. Interrupting the ossicular chain, or otherwise immobilizing the ossicular chain, to prevent this retrograde sound transmission permits significant enhancement of the gain applied to the amplified electrical signal transmitted to the stapes or inner ear. In addition, less mechanical energy is required to transmit the acoustic energy to the interrupted ossicular chain or cochlea than when the ossicular chain remains intact. Accordingly, this method and apparatus reduces power consumption and frequent battery replacement for implantable hearing assistance systems.

DETAILED DESCRIPTION OF THE PREFERRED EMBODIMENTS

Figure 1:
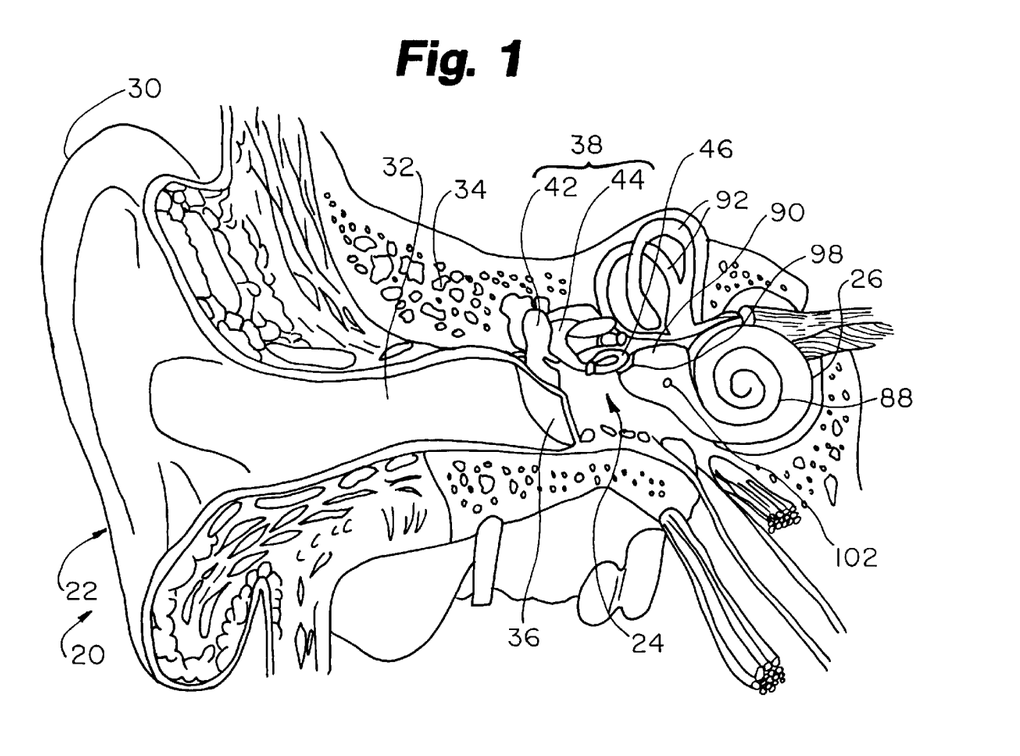
FIG. 1 is a plan view of an auditory system of a human subject.

The ear is the auditory organ of the body. As shown in FIG. 1, ear 20 includes outer ear 22, middle ear 24, and inner ear 26. Outer ear 22, in turn, includes the pinna 30, and exterior auditory canal (external acoustic meatus) 32 extending up to and including tympanic membrane 36. The pinna 30 is the ear flap and is visible on the exterior of the head. The exterior auditory canal extends through temporal bone 34.

Middle ear 24 begins at the interior terminus of exterior auditory canal 32, the tympanic membrane 36. Middle ear 24 includes the interior side of tympanic membrane 36 and ossicular chain 38. Ossicular chain 38, in turn, includes malleus (hammer) 42, incus (anvil) 44, and stapes (stirrup) 46.

Figure 2:
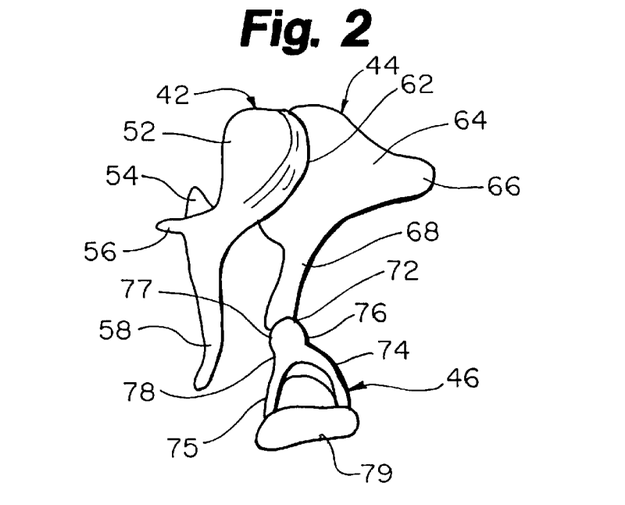
FIG. 2 is an enlarged plan view of an ossicular chain of the auditory system of FIG. 1.

As best seen from FIG. 2, malleus 42 includes head 52, lateral process 54, anterior process 56, and manubrium 58. Malleus 42 attaches to tympanic membrane 36 at manubrium 58. Incus 44 articulates with malleus 42 at incudomalleolar joint 62 and includes body 64, short crus 66, and long crus 68. Stapes 46 articulates with incus 44 at incudostapedial joint 72 and includes posterior crus 74, anterior crus 75, capitulum 76, and base (foot plate) 79. Capitulum 76 of stapes 46, in turn, includes head 77 and neck 78.

The base 79 of stapes 46 is disposed in and against a portion of the inner ear 26. Inner ear 26 includes cochlea 88, vestibule 90, and semicircular canals 92. Base 79 of stapes 46 attaches to oval window 98 on vestibule 90. Round window 102 is present on a more basal portion of vestibule 90. Oval window 98 and round window 102 are considered a portion of cochlea 88 in this patent application.

Sound waves are directed into exterior auditory canal 32 by outer ear 25. The frequencies of the sound waves may be slightly modified by the resonant characteristics of exterior auditory canal 32. These sound waves impinge upon tympanic membrane 36, thereby producing mechanical tympanic vibrations. The mechanical energy of the tympanic vibrations is communicated to inner ear organs cochlea 88, vestibule 90, and semicircular canals 92, by ossicular chain 38. Thus, tympanic membrane 36 and ossicular chain 38 transform acoustic energy in exterior auditory canal 32 to mechanical energy at tympanic membrane 36.

Normally, tympanic vibrations are mechanically conducted through malleus 42, incus 44, and stapes 46 to oval window 98. Vibrations at oval window 98 are conducted into the fluid-filled cochlea 88. These mechanical vibrations generate fluidic motion, thereby transmitting hydraulic energy within cochlea 88. Receptor cells in cochlea 88 transmit the fluidic motion into neural impulses, which are transmitted to the brain and perceived as sound. Pressures generated in cochlea 88 by fluidic motions are also accommodated by round window 102. Round window 102 is a second membrane-covered opening between cochlea 88 and middle ear 24.

Hearing loss due to damage in cochlea 88 is referred to as sensorineural hearing loss. Hearing loss due to an inability to conduct mechanical vibrations through middle ear 24 is referred to as conductive hearing loss. Some patients have an ossicular chain 38 which lacks resiliency. Ossicular chains with insufficient resiliency are either inefficient or totally fail to transmit mechanical vibrations between tympanic membrane 36 and oval window 98. As a result, fluidic motion in cochlea 88 is attenuated and receptor cells in cochlea 88 fail to receive adequate mechanical stimulation. Damaged elements of ossicular chain 38 may further interrupt transmission of mechanical vibrations between tympanic membrane 36 and oval window 98.

Figure 3:
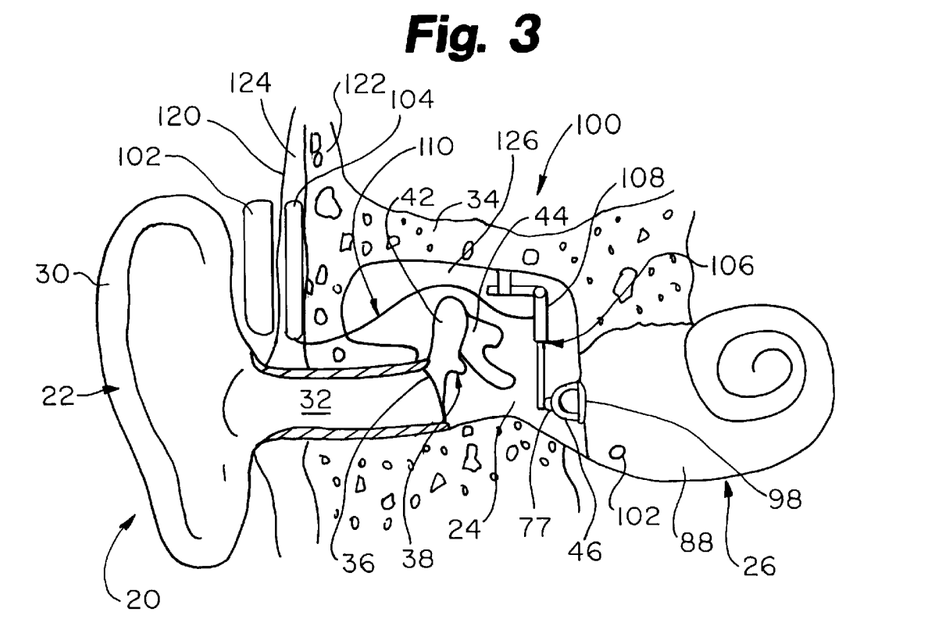
FIG. 3 is a sectional view of an auditory system of a human subject incorporating a first embodiment of an implantable hearing system of the present invention.

A partially implantable hearing assistance system 100 of the present invention for assisting a hearing impaired person is shown generally in FIG. 3 as disposed within ear 20. It is recognized, however, that system 100 may be a dual system suitable for use with either one or both of a patient's ears. System 100 includes an externally-mounted microphone 102, an internal amplifier/signal processor 104, a transducer 106, and frame assembly 108. Electrical connection 110 extends from internal signal processor 104 to transducer 106. A power supply or battery is incorporated into either external microphone 102 or internal signal processor 104.

External microphone 102 is a conventional microphone or other electromechanical device for converting acoustic sound energy into an electrical signal. In one embodiment external microphone may be a handheld or other similarly configured radio frequency linked system operatively coupled with other components of the hearing assistance system. In another embodiment, external microphone 102 is shaped and sized for removable attachment about the ear 20, exterior to skin 120. Internal amplifier 104 includes signal processing circuitry and is either directly electrically connected to microphone 102 through skin 120 or includes a coil transformer for electromagnetically receiving an electrical signal from external microphone 102. Internal amplifier 104 is preferably attached to the patient's skull below skin 122 subdermally within space 124. Both microphone 102 and amplifier 104 are miniature electronic modules well known in the art of hearing assistance systems.

Transducer 106 is disposed within middle ear space 24 and secured against a wall of middle ear space 24 or within mastoid cavity 126 against mastoid bone 34 with frame assembly 108 using one or more fasteners. Finally, transducer 106 is operatively connected to stapes 46. Electrical connection 110, which extends from amplifier 104 to transducer 106, operatively communicatively couples transducer 106 to amplifier 104.

With system 100, acoustic sound vibrations impinging on or about outer ear 22 are received by microphone 102 and converted to an electrical signal and transmitted to amplifier 104. After amplification and modulation, the electrical signal is communicated to transducer 106 via electrical connection 110. In response to the electrical signal, transducer 106 produces an acoustic vibratory signal that is applied to stapes 46 and ultimately, cochlea 88 via oval window 98. Microphone 102, amplifier 104, and transducer 106 and their communication with each other may be of a type generally known to those skilled in the art, although improved transducer means are contemplated within the scope of this invention to facilitate improved implant procedures, to minimize invasiveness, and to improve the reliability of the transducer.

Finally, system 100 and the method of the present invention includes introducing and maintaining a mechanical feedback barrier to prevent mechanical or acoustic feedback from transducer 106 to microphone 102. This feedback barrier is preferably implemented by interrupting ossicular chain 38. However, freezing movement of ossicular chain 38 or otherwise isolating microphone 102 and transducer 106 from mechanical/acoustic feedback through ossicular chain 38 can also provide the necessary barrier. In addition, the feedback barrier can be accomplished through various sound dampening and sound isolation materials and/or techniques placed appropriately about, or between, one or more portions of the ossicular chain.

As shown in FIG. 3, ossicular chain 38 including malleus 42, incus 44, and stapes 46 has been interrupted by disconnecting incus 44 from stapes 46. This interruption creates a barrier to prevent mechanical feedback of acoustic sound energy from transducer 106 through ossicular chain 38 and external auditory canal 32, to microphone 102. Of course, the disarticulation of ossicular chain 38 could occur any place between tympanic membrane 36 (umbo) and transducer 106.

In addition, the transducer 106 can be directly coupled to oval window 98 or round window 102 of cochlea 88 by prior removal of stapes 46. In that embodiment, removal of stapes 46 acts to disarticulate the ossicular chain 38 to prevent feedback and permits malleus 42 and incus 44 to remain in place. Maintaining a connection of at least malleus 42 (and optionally incus 44) to tympanic membrane 36 may also aid in preventing damage from acoustical trauma, since maintaining malleus 42 further enables the natural musculoskeletal defense mechanisms to protect against acoustical trauma.

While removal of ossicular chain 38 has taken place in some prior methods and systems, such removal typically occurs to solve middle ear conduction-type hearing loss problems, or to remove diseased tissue and ossicular bones. Sensorineurally impaired patients have hearing impairments not caused by dysfunction of the middle ear conduction chain, i.e. ossicular chain 38. Accordingly, sensorineural impairments do not dictate removal of ossicular chain 38. In fact, some in the art believe it unethical, or at least inappropriate, to remove a healthy ossicular chain to remedy a hearing impairment. Accordingly, removing or freezing movement of a portion of ossicular chain 38, or otherwise isolating ossicular chain 38 from an implantable middle ear system, such as system 100, in sensorineurally impaired patients is a unique and counter-intuitive solution to reduce acoustic feedback and improve the gain of the hearing assistance system.

While maintaining ossicular chain 38 intact (in order to preserve a healthy ossicular chain 38 despite a hearing impairment) may appear to be less intrusive, a method of the present invention recognizes that unconditionally maintaining the chain can dramatically reduce the gain achieved by the implantable middle ear hearing assistance system due to the feedback phenomenon described above. In this manner, the choice to maintain ossicular chain 38 can actually impede improving hearing in hearing impaired patients, particularly those with sensorineural impairment. However, in certain circumstances according to each patient's middle ear morphology, this invention may not be limited to the class of patients which only includes those suffering from sensorineural impairment. Accordingly, the method of the present invention interrupts ossicular chain 38 to prevent feedback, particularly for sensorineurally impaired patients.

Figure 4:
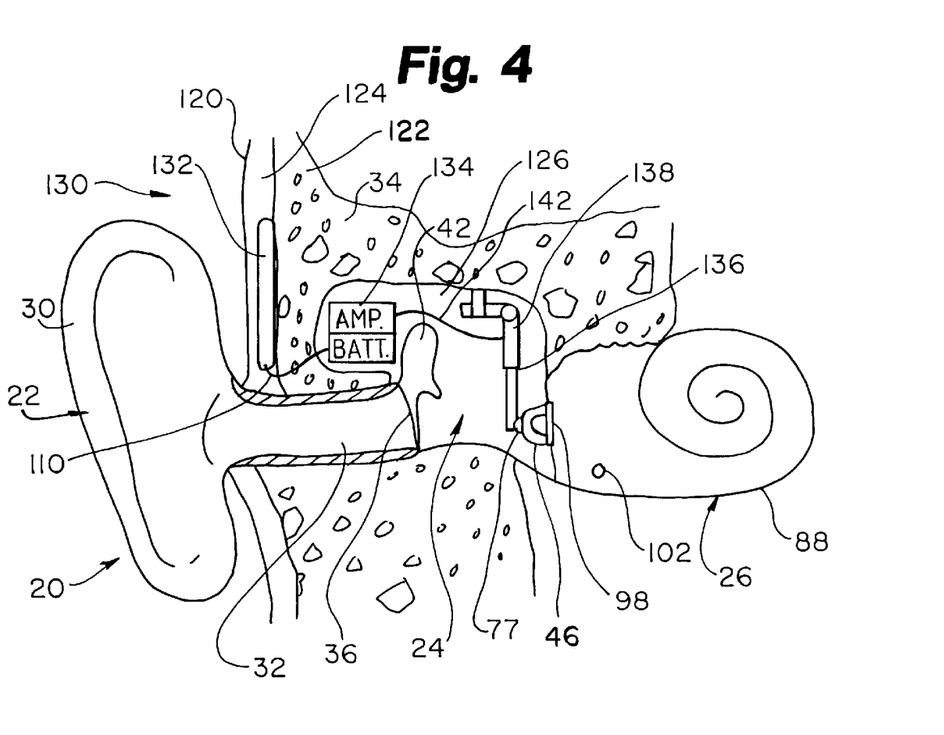
FIG. 4 is a sectional view of an auditory system of a human subject incorporating a second embodiment of an implantable hearing system of the present invention.

Another hearing assistance system 130 of the present invention is shown in FIG. 4. System 130 includes electromechanical device 132 (e.g. microphone), amplifier/signal processor 134, transducer 136, and frame assembly 138 with electrical connections 140 and 142. Microphone 132 has features and attributes similar to microphone 102, except for its implantation below skin 120 subdermally. Signal processor 134 includes an amplifier and signal processing characteristics for amplifying and filtering an electrical signal from microphone 132. A battery may be incorporated with signal processor 134 as shown, or optionally incorporated externally adjacent ear 120, or incorporated with microphone 132. Transducer 136 has features and attributes similar to transducer 106 and is, likewise, connected to stapes 46 via head 77. As in the embodiment of FIG. 3, transducer 136 can alternatively be operatively coupled to round window 102 or oval window 98 of cochlea 88. Signal processor 134 is secured to the mastoid bone 34 within cavity 126. Electrical connection 140 extends between microphone 132 and processor 134 while electrical connection 142 extends between, and electrically couples processor 134 and transducer 136. As shown in FIG. 4, incus 44 was removed from ossicular chain 38 to introduce and maintain a feedback barrier against transmission of mechanical sound energy through ossicular chain 38 from transducer 136 to external auditory canal 32, and ultimately, microphone 132. Of course, as earlier noted, other portions can be removed from ossicular chain 38 in place of removing incus 44 to effect the disarticulation and interruption of ossicular chain 38 to prevent acoustic feedback.

This method and system 132 enjoys advantages and features similar to system 100 as a result of the introduction of an acoustic feedback barrier between microphone 132 and transducer 136.

Figure 5:
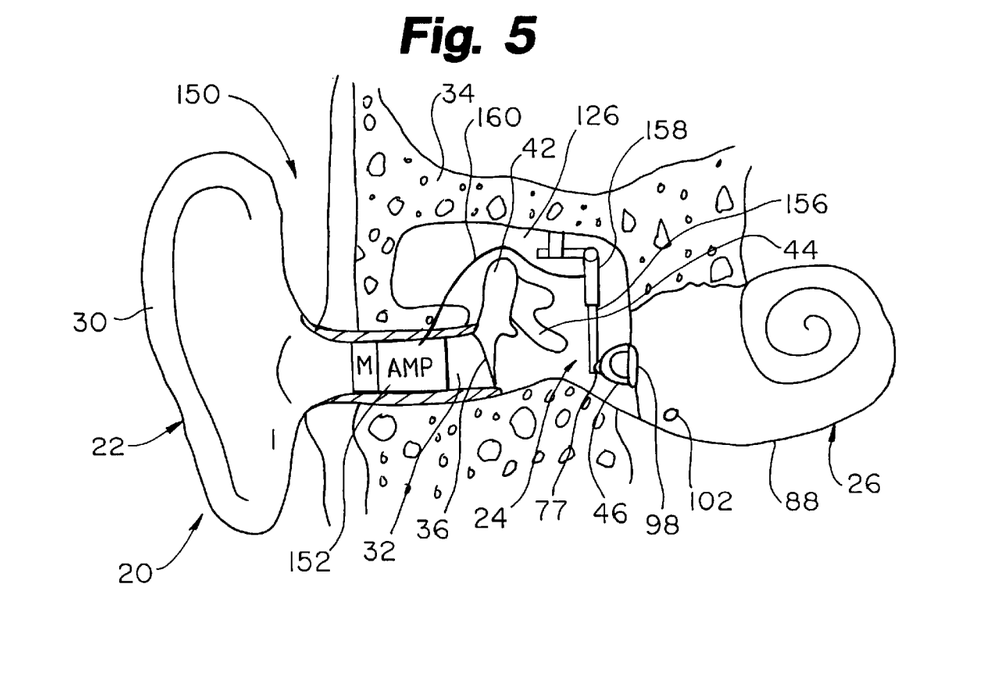
FIG. 5 is a sectional view of an auditory system of a human subject incorporating a third embodiment of an implantable hearing system of the present invention.

Another partially implantable hearing system 150 of the present invention is shown in FIG. 5. System 150 includes a single unit implantable device 152, including a microphone, amplifier, and battery. System 150 further includes transducer 156, frame assembly 158, and electrical connection 160. Device 152 is removably secured within the auditory canal, for example in external auditory canal 32, while transducer 156 is supported within the middle ear cavity 24 by connection assembly 158 secured against mastoid bone 34 within cavity 126. As before, transducer 156 is secured to head 77 of stapes 46 or, alternatively, secured to the oval or round windows of cochlea 88 in the absence of stapes 46. As in the other systems 100 and 130, disarticulation of the ossicular chain 38 creates a feedback barrier to prevent a retrograde transmission of sound energy from the transducer 136 through the external auditory canal 32 to microphone of device 152. As shown, ossicular chain 38 has been interrupted, or disarticulated, by separating incus 44 from stapes 46. However, disarticulation could take other forms, including removal of incus 44, removal of malleus 42 or removal of stapes 46, or any combination thereof. Moreover, as discussed further below in connection with FIG. 9, disarticulation can include cutting or removing a portion of the incus to interrupt the ossicular chain, as well as other techniques.

Figure 6:
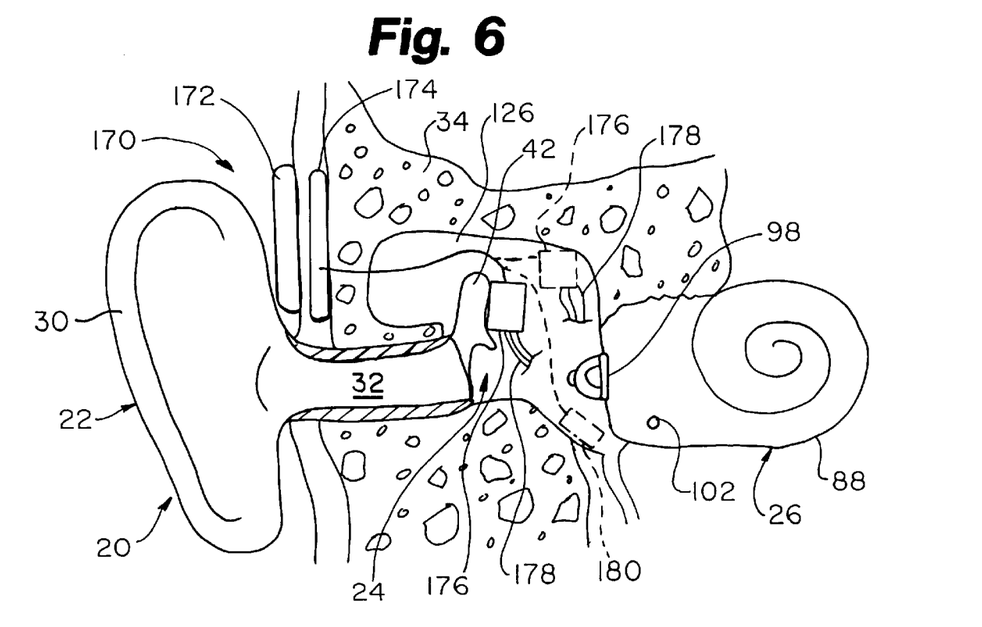
FIG. 6 is a sectional view of an auditory system of a human subject incorporating a fourth embodiment of an implantable hearing system of the present invention.

In another embodiment of the present invention shown in FIG. 6, a hearing assistance system 170 includes features and attributes similar to system 100 shown in FIG. 3 by having an external microphone or electromechanical device 172 and an internal amplifier 174. However, in system 170, an electrical stimulator, such as a piezoelectric accelerometer 176 is mounted within mastoid cavity 126, as shown in phantom, or on the head of malleus 142. Electrical stimulator 176 includes leads 178 for electrical connection to various portions of cochlea 88 for electrical stimulation thereof to produce neural impulses corresponding to the acoustic sound received by microphone 172, as known in the art. Electrical connection 180 operatively couples amplifier 174 to stimulator 176. Finally, alternatively to electrical stimulator 176, mechanical stimulator 180 can be operatively coupled to round or oval window of cochlea 88. As shown in FIG. 6, as in the other of the present invention systems 100, 130, and 150 a feedback barrier is introduced between microphone 172 and stimulator 176 or 180 by disarticulation of ossicular chain 38. Disarticulation of the ossicular chain is accomplished by removal of the stapes 46 or separation of ossicular chain 38 elements (without their removal). Of course, the other microphone and amplifier combinations as shown in FIGS. 4 and 5 can be implemented with an electrical stimulator, such as stimulator 176 (or the alternative mechanical stimulator 180).

Implementing the method of the present invention in the embodiment of FIG. 6 insures no inadvertent acoustic/mechanical feedback occurs through ossicular chain 38 to microphone 172 from stimulator 176, 180 or from cochlea oval window 98 even though direct stimulation of cochlea 88 occurs apart from ossicular chain 38.

Figure 7A:
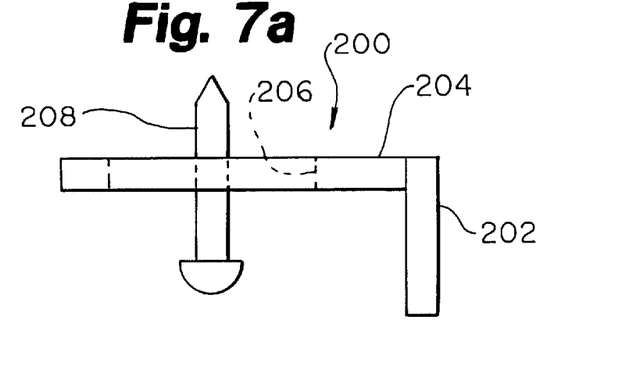
FIG. 7A is a plan side view of a mounting bracket of the present invention.
Figure 7B:
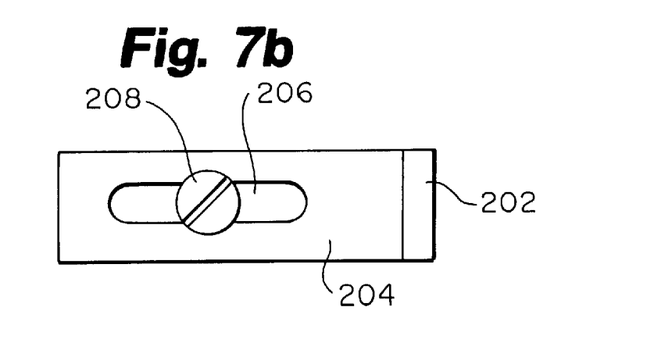
FIG. 7B is a plan top view of a mounting bracket of the present invention.
Figure 7C:
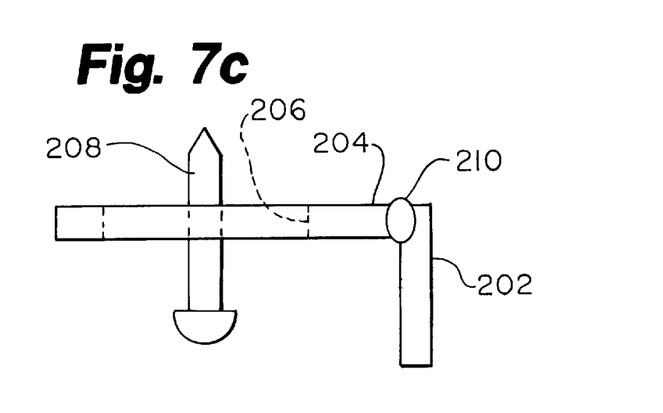
FIG. 7C is a plan side view of a modified mounting bracket of the present invention.

FIGS. 3–5 each show a mounting bracket (108, 138, 158) for placing a transducer in contact with an auditory element of the stapes. While brackets known in the art can be used, the method and systems of the present invention may also use a bracket of the type similar to that shown in FIGS. 7A–7C. FIGS. 7A, 7B, and 7C show a bracket system 200 having a transducer 202 attached to the single bracket support 204. The single bracket support 204 includes an opening 206. A bone screw 208 or similar attaching means passes through the oblong opening 206 and allows for independent adjustment of the distance between the support mounting screw 208, which is typically a bone screw, and the transducer 202. Such adjustment allows flexibility in that the single bracket support can be mounted with respect to different auditory elements, such as the malleus 42 and the stapes 46, respectively, in a patient population having varying anatomical features within the middle ear 24.

The shape of single bracket support 204 in this embodiment is more or less a flat plate. The transducer 202 is coupled to the flat plate either adhesively, mechanically or otherwise, to produce a single component. It should be noted that other configurations are possible, depending on patient anatomy and other factors. A generally L-shaped bracket, a rectangular-shaped bracket, or any other shaped bracket that facilitates mounting of transducer 202 can be used in place of the single bracket support 204. The bone screw 208 couples the single bracket support 204 to the mastoid bone 34. Other types of fastening techniques can also be used. For example, single bracket support 204 can be shaped with a flange that could be attached to the mastoid bone 34. The single bracket support 204 can be moved linearly and rotated with respect to the bone screw 200 to position the transducer 202 in a selected position with respect to one of the elements of the middle ear.

FIG. 7C shows an embodiment having a universal connector 210 placed between the transducer 202 and the single bracket support 204. The universal connector 210 may also be placed between the two portions of the single bracket support 204. The universal connector 210, such as a ball and socket joint, allows further adjustability and 360-degree movement to position the transducer 202 against respective auditory elements 42 and 46.

As shown in later FIGS. 8 and 9, bracket system 200 can include multiple bracket supports 204 each having a universal connector 210 for adjustability. In addition, the bracket systems 200 can include multiple slots such as slot 206, laterally spaced from each other and having different lengths, to permit flexibility in selecting the length at which bracket support 204 extends outwardly from its point of attachment to the mastoid bone or middle ear structure.

As shown in prior FIGS. 3–5, a fastener, such as bone screw 208 is attached to the mastoid bone 34 to secure the bracket 200 within middle ear space 24 and transducer 202 adjustably in contact with stapes 46. Of course, bracket 202 also permits transducer 202 to be adjustably in contact with the malleus 42 via universal joint 210. The various transducer and mounting means of the invention facilitate a trans-canal implant procedure by which portions of the device of the invention are implanted, in one embodiment, through the auditory canal and the tympanic membrane into the middle ear.

Figure 8:
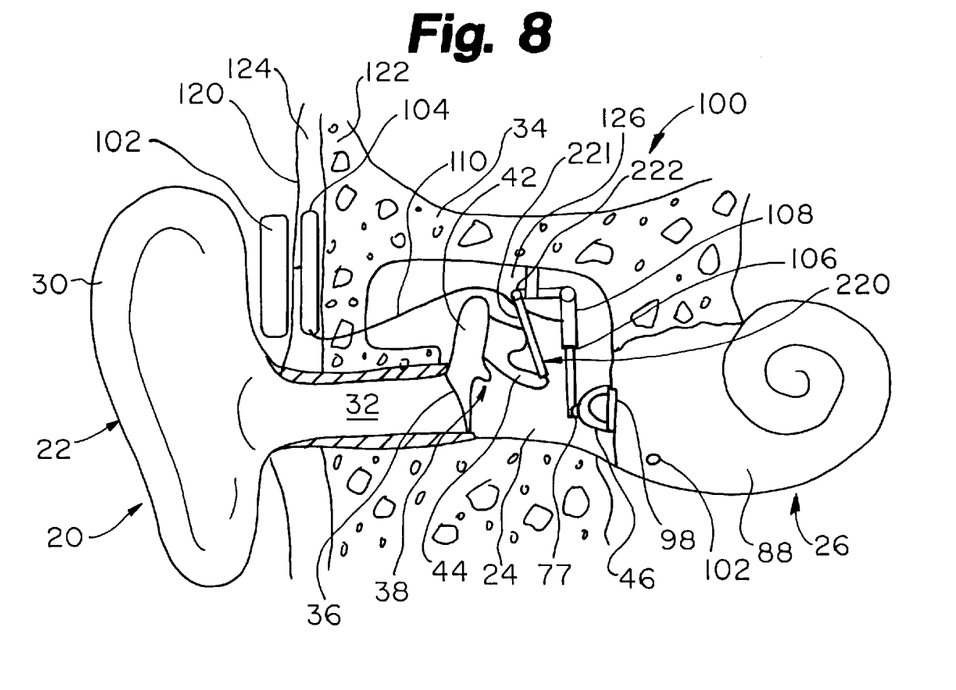
FIG. 8 is a sectional view of an auditory system of a human subject incorporating a modification of the embodiment of FIG. 3.

Another system 220 and method of the present invention is shown in FIG. 8. System 220 includes system 100 as shown in FIG. 3 and further includes securing incus 44 into a fixed position within the middle ear. Accordingly, system 200 further includes additional bracket support 221 (with universal joint 222) affixed to long process 68 of incus 44. Bracket 221 secures incus in a position separated from stapes 46 to prevent retrograde transmission of sound along the ossicular chain. Bracket 221 could also be implemented to secure incus 44, malleus 42, or stapes 46 in a configuration, where none of the auditory elements (incus, malleus, stapes) have been removed nor separated from each other, to effectively freeze the ossicular chain preventing transmission of sound along the chain. In this latter configuration, incus 44 remains connected to stapes 46 (as shown in FIG. 1) and bracket 221 is connected to malleus 42, incus 44, or stapes 46 with sufficient tension to freeze motion of the ossicular chain to establish a mechanical feedback barrier.

Figure 9:
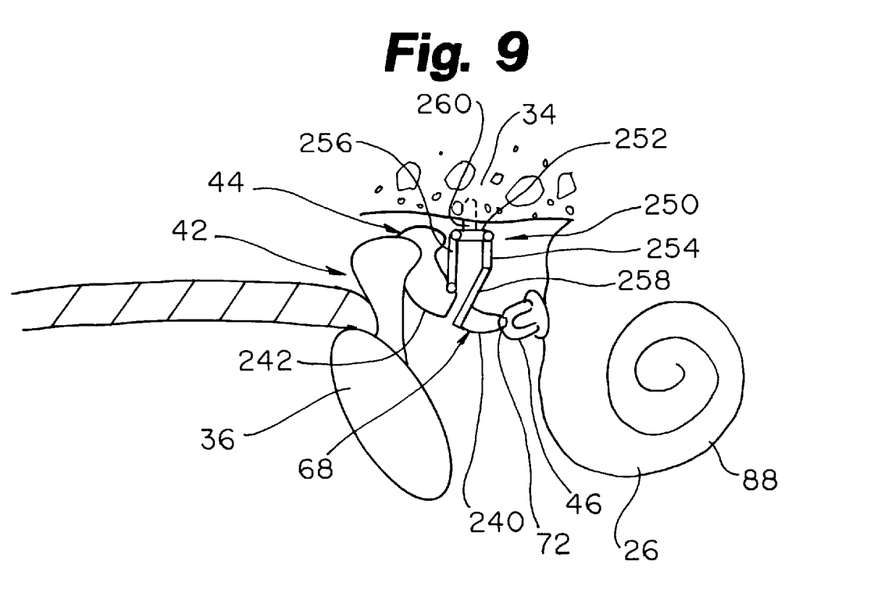
FIG. 9 is a sectional view of an auditory system of a human subject incorporating another embodiment of an implantable hearing system and method of the present invention.

Another method and system of the present invention for maintaining a mechanical barrier against feedback is illustrated in FIG. 9. As shown in FIG. 9, malleus 42, incus 44 and stapes all remain within middle ear space 24. However, incus 44 includes long process 68, which has been surgically cut (e.g. by laser or other means) into first portion 240 and second portion 242. As further shown in FIG. 9, system 250 of the present invention includes bracket support frame 252, bracket extensions 254 and 256, transducer 258 and fastener 260.

Implementing bracket system 250 in a method of the present invention includes interrupting the ossicular chain to prevent feedback by cutting incus 44 into two separate portions 240 and 242. This method can be used in conjunction with the hearing systems of FIGS. 2–5 and 8 to establish a mechanical feedback barrier wherein cutting incus 44 is substituted for: (1) removing incus 44; (2) separating incus 44 from the stapes 46 or malleus 42; or (3) any other method of interrupting the ossicular chain, such as freezing or fixing the position of the ossicular chain without cutting or separating elements of the chain.

Next, the method includes mounting bracket system 250 against mastoid bone 34 with fastener 260 and manipulating bracket extension 254 to place transducer 258 in contact with portion 240 of long process 68 of incus 44. Next, transducer 258 is operatively secured or positioned against the exposed end of portion 240 with an adhesive or other known fastening means. The cut through long process 68 of incus 44 is made so that a separation of at least about 2 to 3 millimeters is maintained between the ends of incus portions 242 and 240, accounting for a transducer thickness of about 0.5 millimeters mounted on the end of incus portion 240. This separation distance prevents mucosal growth or bone re-growth that could otherwise act to rejoin incus portions 240 and 242.

With this configuration, transducer 258 can receive an electrical signal and transmit to incus portion 240 a sound vibration signal for delivery to inner ear 26 via stapes 46. Transducer 258 receives its signal from an electromechanical device (e.g, microphone) and/or amplifier disposed in one of the configurations shown in FIGS. 2–5, 8, and 10.

This method preserves incudostapedial joint 72 so that natural transmission occurs from incus 44 to stapes 46 and so that in the event the procedure needs to be reversed, incudostapedial joint need not be re-created but rather incus portions 240 and 242 can simply be fused together. This method also preserves the lenticular process on stapes 46. In short, this method permits interruption of the ossicular chain in a minimally invasive and reversible manner, while enhancing hearing assistance.

While feedback can be prevented with portion 240 of incus 44 being merely separated from portion 242, it is preferred, as shown, to optionally further secure incus portion 242 into a fixed position with bracket extension 256 to insure incus portion 242 remains separated from portion 240 at an adequate minimum separation distance (e.g. about 2–3 millimeters) to prevent tissue reconnection or inadvertent contact between incus portions 240 and 242.

Figure 10:
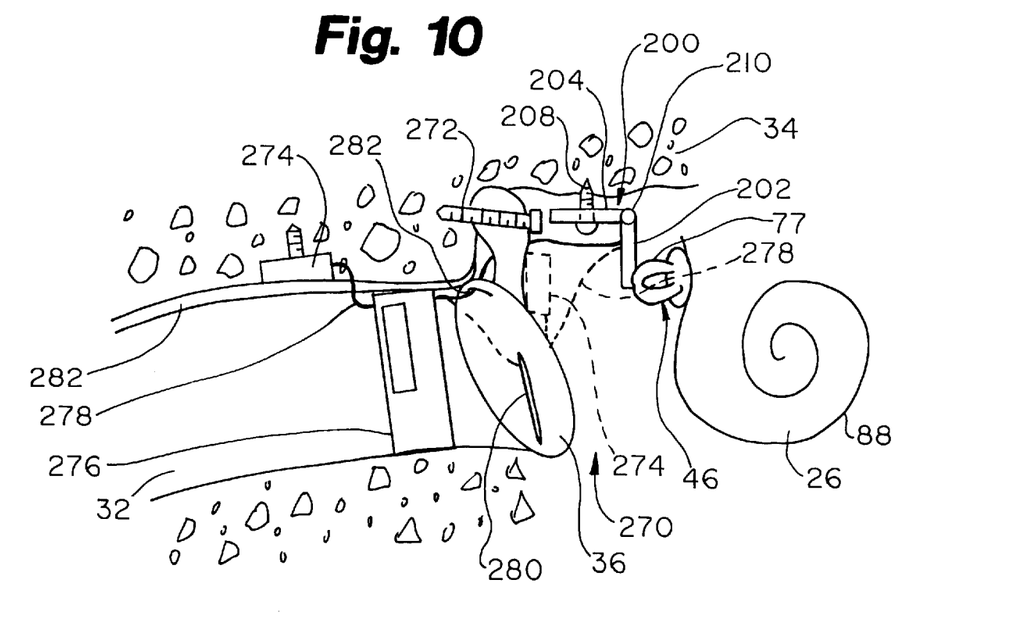
FIG. 10 a sectional view of an auditory system of a human subject incorporating another embodiment of an implantable hearing system and method of the present invention.

As shown in FIG. 10, a human auditory canal is depicted with system 270 and a method of the present invention incorporated therein. System 270 for implementing a method of the present invention includes bracket system 200 (see FIGS. 7A–7C) having transducer 202, bracket support 204, positioning slot 206 (not seen in FIG. 10), fastener 208, and universal connector 210. System 270 further includes malleus fastener 272, microphone 274, amplifier/electronics unit 276, lead wires 278. Finally, the method includes formation of slit or hole 280 in tympanic membrane 36.

First, in this method, microphone 274 preferably is located along external auditory canal 24 in contact with the canal wall 282. This configuration takes advantage of the known sound filtering and amplification characteristics and localization effects of the outer ear 22 (including the structure shown in FIG. 1 extending from the pinna 30 to the tympanic membrane 36) of the human auditory system. This microphone location can be implemented to substitute for any of the microphone locations of the systems shown and described relative to FIGS. 2–6 and 8–9. Microphone 274 is preferably a directional microphone which receives sound transmission traveling inwardly through the external auditory canal 32 while excluding sound transmission traveling outwardly through the external auditory canal 32.

In addition, as will be further described later, microphone 274 can be located within middle ear space 24 behind tympanic membrane 36, preferably on malleus 42 as shown in phantom in FIG. 10. When microphone 274 is an acoustic microphone, this placement also takes advantage of the sound filtering, amplification, and localization effects of outer ear 30.

Second, amplifier/electronics unit 276 is placed in external auditory canal 32 or another location available (e.g. pectoral, or outside skull) to avoid a mastoidectomy procedure. Placement of amplifier/electronics unit at a pectoral location permits the use of long life batteries having a size normally unsuitable for middle ear implantation and/or permits easier battery replacement. Amplifier 276 is electrically connected to microphone 274 with lead wires 278 (shown in phantom for microphone placement on malleus 42). Lead wires 278 pass through slit 282 (or slit 280) of tympanic membrane 36 for connection to transducer 202.

The following method of insertion is used for implanting at least transducer 202, electromechanical device 274 (in phantom in FIG. 10) or any other component hearing assistance system 270 within middle ear space 24.

First, transducer 202 is affixed to a mounting bracket prior to insertion in the middle ear. The mounting bracket system 200 preferably includes a universal joint 210 disposed between a first elongate portion (support 204) and a second elongate portion (transducer 202). The second portion 202 commonly includes both a support and the transducer affixed together.

Figure 11:
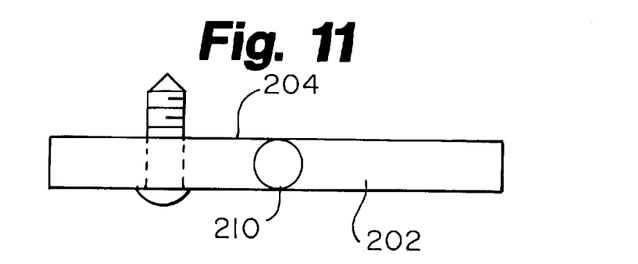
FIG. 11 is a plan side view of a mounting bracket of the present invention manipulated to a pre-insertion position.
Figure 12:
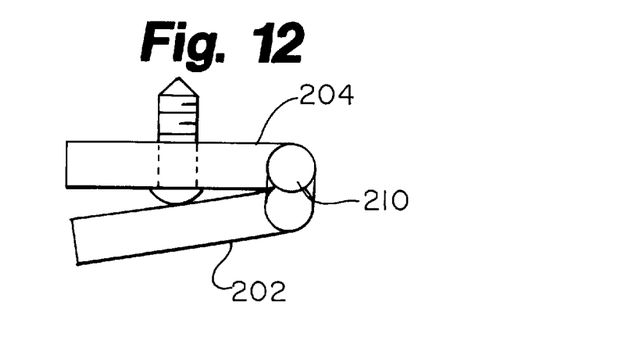
FIG. 12 is a plan side view of a mounting bracket of the present invention manipulated to a pre-insertion position.

Prior to insertion in the middle ear, first portion 204 and second portion 202 of mounting bracket system 200 are manipulated to be aligned in an elongate configuration generally parallel along a single axis. The configuration can include either arranging first portion 204 and second portion 202 of the mounting bracket 200 in a side-by-side relationship generally parallel to each other as shown in FIG. 11, or as shown in FIG. 12, arranging first portion 204 and second portion 202 of mounting bracket 200 in an end-to-end relationship (aligned generally parallel along a single axis). In general, first portion 204 and second portion 202 need not be generally parallel but can be in any configuration (e.g. 45 or 90 angle) that facilitates insertion of mounting bracket 200 into the middle ear space 24 through tympanic membrane 36.

Next, using surgical techniques known to those skilled in the art, a low profile entry slit or hole 280 is created in tympanic membrane 36. With the mounting bracket system 200 and transducer in one of the above low profile configurations (see, e.g., FIG. 11), mounting bracket 200 is inserted into and through slit 280 in tympanic membrane 36. After first portion 204 and second portion 202 of mounting bracket 200 are reconfigured into an operative in-use configuration (e.g. 30, 60 or 90 angles), bracket 200 is then mounted against a wall of the middle ear space or against mastoid bone 34 as shown. In a system, such as that shown in FIG. 10 (microphone 274 and electronics unit 276 external to middle ear), middle ear implantation of transducer 202 via tympanic membrane 36 avoids a mastoidectomy. After insertion of the transducer 202 through slit 280, tympanic membrane 36 will heal appropriately.

This method permits insertion of a device such a bracket/transducer combination into the middle ear without a mastoidectomy where the bracket/transducer can be deployed in the middle ear space in a configuration different than the configuration used for insertion through tympanic membrane.

Of course, in the embodiment where microphone 274 is mounted behind tympanic membrane 36 on malleus 42 (shown in phantom), microphone 274 can be inserted through tympanic membrane 26 without a mounting bracket 200. Instead, microphone 274 may include adhesive means for mounting to malleus 42 or other fastening system.

Moreover, the method of insertion/implantation through tympanic membrane 36 according the present invention is not limited to the use of bracket 200. Accordingly, any transducer or component of a hearing assistance system can be inserted through tympanic membrane 36 without a bracket like bracket system 200 for implantation in middle ear 24. For example, the other systems shown in FIGS. 2–6, 8–9 that have at least a transducer or electromechanical device or component of a hearing assistance system can be implanted with the just described method of insertion instead of using a mastoidectomy.

In addition, insertion through tympanic membrane 36 can optionally be combined with other features of the present invention such as securing an auditory element into a fixed position. Accordingly, as shown in FIG. 10, malleus 42 is secured in a fixed position by fastener 272 to prevent transmission of feedback sound energy along the ossicular chain. Of course, other fastening means such as brackets, like bracket system 200, sutures, bone cement and adhesives can be used.

In addition, the cochlea stimulator embodiments of FIG. 6 can be modified so that microphone 172 is replaced with a microphone located behind the tympanic membrane 36 within middle ear space 24, such at microphone 274 (shown in phantom in FIG. 10) attached to malleus 42.

The method and system of the present invention improves hearing assistance for the hearing impaired in implantable hearing systems using a microphone by neutralizing acoustic feedback through the ossicular chain and external auditory canal. The method can be employed in virtually all combinations of implantable systems having microphones located externally, subdermally, or within or along the external auditory canal. Elimination of acoustic feedback through the ossicular chain produces better gain in these systems, and reduces power consumption since less mechanical force is required to transmit acoustic signals into the inner ear (via stapes or not) with an interrupted ossicular chain. Moreover, the methods of the present invention are minimally invasive procedures using tympanic insertion of a transducer or mounting bracket and/or reversible procedures using separation of the ossicular chain without removal of any auditory elements or without dismembering any joints such as the incudostapedial joint.

Figure 13:
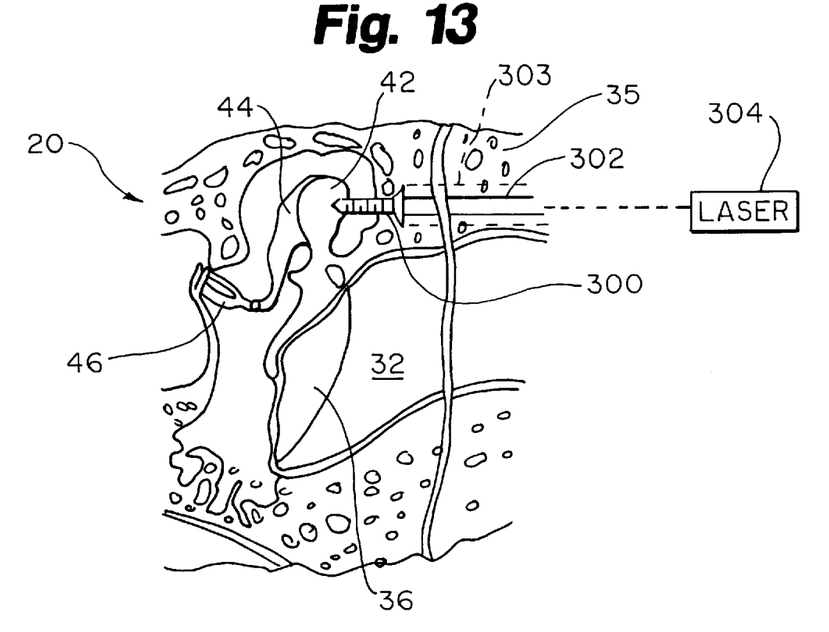
FIG. 13 is a schematic plan view of a malleus fixation method of the present invention.

A further method and system of ossicular chain fixation of the present invention for reducing mechanical feedback is shown in FIG. 13. FIG. 13 shows auditory system 20 including external auditory canal 32, bone 35 (e.g. temporal bone), tympanic membrane 36, malleus 42, incus 44, and stapes 46. In this method, hole 302 is drilled through bone 35 (preferably temporal bone near the zygomatic root) until malleus 42 is visualized. Next, laser 304 is used to cut a hole in the head of malleus 42 for receiving fastener 300 (e.g., screw, rivet, pin, etc.). Fastener 300 is then inserted into and through hole 300 and securely fixed into head of malleus 42 with a portion (e.g. Head) of fastener 30 remaining within bone 35. This arrangement securely fixes head of malleus 42 to bone 35, thereby restraining movement of malleus 42 and thereby reducing and/or preventing mechanical feedback through ossicular chain according the method of the present invention previously described. As seen in FIG. 13, in this embodiment, the elements of the ossicular chain are not separated from each other although separation of one or more elements of the ossicular chain may optionally be done in combination with fixation of malleus by fastener 300.

In addition, other methods of access to malleus 42 for fixing fastener 300 thereon can be used such as a mastoidectomy, or access through a wall of the external auditory canal, or other methods available to those skilled in the art. FIG. 13 also shows hole 303 in phantom to represent the possible need for a wider hole to accommodate a head of fastener 300 as necessary.

Figure 14:
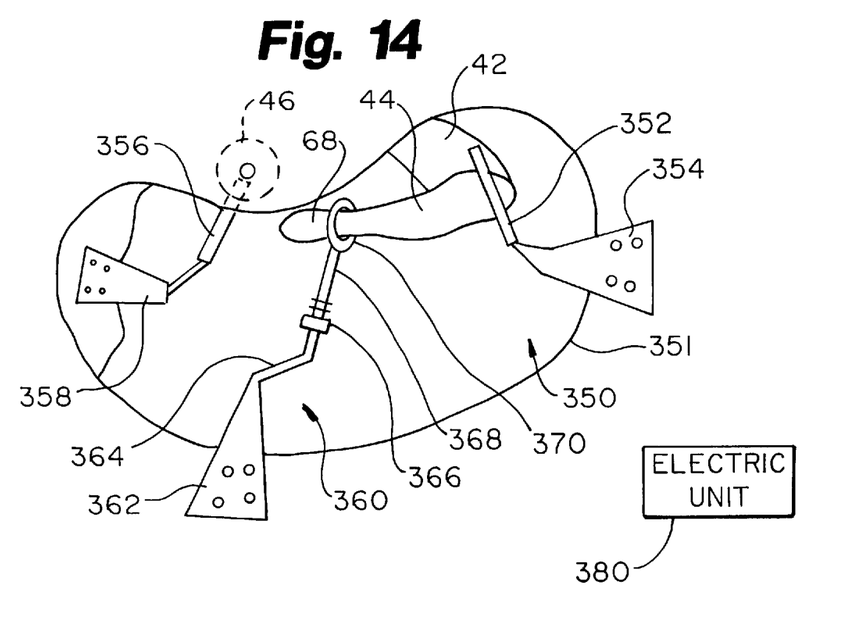
FIG. 14 is a schematic view of an incus separation and fixation method of the present invention.

Finally, in another embodiment of a method of fixation and separation of the ossicular chain of the present invention, a combined fixation and separation system 350 operates to separate incus 44 from stapes 46 (e.g. at incudostapedial joint) and securely fix incus 44 to restrain its movement. As shown in FIG. 14, system 350 is implemented with malleus 42, incus 44, and stapes 46, all of which are visible (except stapes 46) through an access hole 351 provided by a partial or whole mastoidectomy or other surgical techniques for gaining access to the ossicular chain. System 350 includes sensor 352 with accompanying support bracket 354, stapes driver 356 with accompanying support bracket 358, and incus fixator 360. Fixator 360 includes supporting bracket 362, extension support 364 having a selectively variable position, fastener 366, fixator arm 368 and ring 370.

In use, stapes 46 is separated from incus 44 as shown. Sensor 352 and driver 356 are operatively coupled to malleus 42 and stapes 46, respectively, using known techniques and/or supporting brackets 354 and 358. Sensor 352 and driver 356 are operatively coupled to each other and/or electronics unit 380 via electrical wires, and can omit or include further combinations of intervening signal processing, amplification, filtering and gain compression components as necessary.

Ring 370 of incus fixator 360 is maneuvered about long process 68 of incus 44, operating as a lasso to slip over the free end of incus 44 to effectively grasp incus 44, creating an operative coupling of fixator arm 368 to incus 44. Supporting bracket 362, selectively variable position extension arm 364, and fastener 366 are manipulated into a selected fixed position to maintain incus 44 in a fixed position separated from stapes 46. This arrangement prevents mechanical feedback through the ossicular chain in accordance with the previously described methods of the present invention.

Although the present invention has been described with reference to preferred embodiments, workers skilled in the art will recognize that changes may be made in form and detail without departing from the spirit or scope of the present invention. However, what is disclosed includes as a minimum the following various concepts. A method and apparatus assists a hearing impaired person by introducing and maintaining a mechanical feedback barrier between a microphone and a transducer of an implantable hearing assistance system. In this method, mechanical sound vibrations impinging on the person's body habitus are received with an electromechanical device (e.g. microphone) disposed at a body habitus sound reception site. The body habitus sound reception site can be located within the external auditory canal, or external of the external auditory canal either subdermally or external of the scalp. The mechanical sound vibrations are converted with the electromechanical device to an amplified electrical signal. Next, the amplified electrical signal is delivered to the inner ear with a transducer operatively coupled between the electromechanical device and the middle ear or the inner ear. Finally, a mechanical feedback barrier is introduced and maintained between the sound reception site and the transducer to minimize acoustic feedback therebetween. Preferably, this feedback barrier is established by removing, separating, or fixing, or combinations thereof, a portion of the hearing impaired person's ossicular chain (e.g malleus, incus, or stapes). In another embodiment, a method and apparatus assists a hearing impaired person by introducing and maintaining a mechanical feedback barrier between a microphone and a transducer of an implantable hearing assistance system. In this method, mechanical sound vibrations impinging on the person's body habitus are received with an electromechanical device (e.g. microphone) disposed at a body habitus sound reception site. The body habitus sound reception site can be located within the external auditory canal, or external of the external auditory canal either subdermally or external of the scalp. The mechanical sound vibrations are converted with the electromechanical device to an amplified electrical signal. Next, the amplified electrical signal is delivered to the inner ear with a transducer operatively coupled between the electromechanical device and the middle ear or the inner ear. Finally, a mechanical feedback barrier is introduced and maintained between the sound reception site and the transducer to minimize acoustic feedback therebetween. Preferably, this feedback barrier is established by removing, separating, or fixing, or combinations thereof, a portion of the hearing impaired person's ossicular chain (e.g., malleus, incus, or stapes). In another embodiment, a method and apparatus assists a hearing impaired person by introducing and maintaining a mechanical feedback barrier between a microphone and a transducer of an implantable hearing assistance system. In this method, mechanical sound vibrations impinging on the person's body habitus are received with an electromechanical device (e.g. microphone) disposed at a body habitus sound reception site. The body habitus sound reception site can be located within the external auditory canal, or external of the external auditory canal either subdermally or external of the scalp. The mechanical sound vibrations are converted with the electromechanical device to an amplified electrical signal. Next, the amplified electrical signal is delivered to the inner ear with a transducer operatively coupled between the electromechanical device and the middle ear or the inner ear. Finally, a mechanical feedback barrier is introduced and maintained between the sound reception site and the transducer to minimize acoustic feedback therebetween. Preferably, this feedback barrier is established by removing, separating, or fixing, or combinations thereof, a portion of the hearing impaired person's ossicular chain (e.g., malleus, incus, or stapes).

What is claimed is:

1. A method for assisting hearing for a sensorineurally hearing impaired person comprising:

receiving sound vibrations impinging on the person's body habitus with an electromechanical device disposed at a body habitus sound reception site and converting the sound vibration with the electromechanical device to an amplified electrical signal;

delivering the amplified electrical signal to the inner ear with transducer means operatively coupled between the electromechanical device and the inner ear;

maintaining a mechanical feedback barrier between the sound reception site and the inner ear to minimize feedback therebetween during the receiving and delivering steps.

2. The method of claim 1, wherein the maintaining step further comprises:

interrupting the ossicular chain.

3. The method of claim 2, wherein the interrupting step further comprises:

cutting a portion of the incus to separate the incus into two separate portions that do not contact each other.

4. The method of claim 3, wherein the cutting step is performed with a laser.

5. The method of claim 3, wherein the cutting step is applied to the long process of the incus.

6. The method of claim 3, wherein the cutting step further comprises:

selecting the cutting location on the incus to maintain intact the incudostapedial joint.

7. The method of claim 1, wherein the maintaining step further comprises:

separating a portion of the ossicular chain into separate first and second portions and mounting the transducer on the first portion and maintaining a separation distance between the transducer and the second portion to prevent tissue reconnection between the second portion and at least one of the transducer and the first portion.

8. The method of claim 2, wherein the interrupting step further comprises:

removing only the incus to maintain intact the malleus.

9. The method of claim 1, wherein the receiving step further comprising:

locating the sound reception site of the electromechanical device externally of the skull.

10. The method of claim 1, wherein the receiving step further comprising:

locating the sound reception site of the electromechanical device within the external auditory canal.

11. The method of claim 1, wherein the receiving step further comprising:

locating the sound reception site of the electromechanical device subdermally adjacent the ear.

12. The method of claim 1, wherein the delivering step further comprises:

operatively coupling the electromechanical device to the transducer means with an electromechanical linkage.

13. The method of claim 12, wherein the operative coupling step further comprises:

arranging a connection assembly within the middle ear to secure the electromechanical device and the transducer relative to the cranium and a portion of the ossicular chain.

14. The method of claim 13, wherein the connection assembly further comprises a bracket.

15. The method of claim 13, wherein the connection assembly further comprises a hanger.

16. The method of claim 9, wherein the connection assembly further comprises a combination mounting bracket and removable portion.

17. The method of claim 1, wherein the delivering step further comprises:

operatively connecting the transducer to at least one of a stapes and an incus of the middle ear.

18. The method of claim 1, wherein the transducer comprises a piezoelectric transducer.

19. The method of claim 1, wherein the transducer comprises an electromagnetic transducer.

20. The method of claim 1, wherein the electromechanical device comprises a microphone.

21. The method of claim 1, wherein the electromechanical device comprises a second transducer.

22. The method of claim 1, wherein the electromechanical device further comprises a directional microphone for enhancing sound reception of sound energy traveling into the external auditory canal toward the tympanic membrane and for excluding sound energy traveling outwardly away from the tympanic membrane.

23. The method of claim 1, wherein the electromechanical device and the transducer are arranged into a single unit sound energy processor.

24. The method of claim 23, wherein the receiving step further comprises:
locating the sound reception site subdermally.

25. The method of claim 23, wherein the receiving step further comprises:
locating the sound reception site in the external auditory canal.

26. The method of claim 23, wherein the receiving step further comprises:
locating the sound reception site externally from the scalp.

27. A partially implantable apparatus for improving the hearing of a sensorineural hearing impaired subject without causing feedback through the ossicular chain of the subject, comprising:
an artificial sensing transducer for sensing air conducted signals external to the middle ear;
input and output transducer means adapted for cranial location for mediating mechanical and electrical signals having controlled amplification characteristics, the input and output transducer means having electromechanical linkage means for operatively communicatively coupling the artificial sensing transducer to the inner ear of the subject to transmit signals therebetween without feedback of mechanical sound energy from the inner ear to the artificial sensing transducer through the ossicular chain and the external auditory canal.

28. The apparatus of claim 27, wherein the artificial sensing transducer is configured and arranged for disposition external of the subject's external auditory canal.

29. The apparatus of claim 27, wherein the artificial sensing transducer is configured and arranged for disposition within the subject's auditory canal.

30. The apparatus of claim 27, wherein the transducer is a piezoelectric transducer.

31. The apparatus of claim 27, wherein the transducer is an electromagnetic transducer.

32. The apparatus of claim 27, wherein the electromechanical linkage means further comprises:
a connection assembly adapted to be secured to a portion of the subject's ossicular chain.

33. The apparatus of claim 32, wherein the connection assembly further comprises a bracket.

34. The apparatus of claim 32, wherein the connection assembly further comprises a hanger.

35. The apparatus of claim 32, wherein the connection assembly further comprises a combination mounting bracket and removable portion.

36. The apparatus of claim 27, and further comprising:
means for separating a portion of the ossicular chain to prevent mechanical feedback.

37. A method for assisting hearing for a sensorineurally hearing impaired person comprising:
receiving sound vibrations impinging on a person's body habitus with an electromechanical device disposed at a body habitus sound reception site and converting the sound vibration with the electromechanical device to an amplified electrical signal;
delivering the amplified electrical signal to the inner ear with transducer means operatively coupled between the electromechanical device and the inner ear;
maintaining a portion of the ossicular chain in a fixed position to maintain a mechanical feedback barrier preventing transmission of sound energy along the ossicular chain to minimize sound energy feedback between the inner ear and the sound reception site during the receiving and delivering steps.

38. The method of claim 37, wherein the maintaining step further comprises:
stabilizing the ossicular chain with a mechanical fixator to prevent transmission of sound energy along the ossicular chain.

39. The method of claim 38, wherein the stabilizing step further comprises:
stabilizing an incus of the ossicular chain with the mechanical fixator.

40. The method of claim 37, wherein the maintaining step further comprises:
separating an incus from a stapes of the ossicular chain at the incudostapedial joint and positioning a long process of the incus to prevent unintended reconnection of the incus with the stapes.

41. The method of claim 40, wherein the positioning of incus further comprises:
restraining a portion of the incus apart from the stapes to maintain separation at the incudostapedial joint.

42. The method of claim 41, wherein the restraining step further comprises:
preserving the incus by performing the separating step without cutting the incus.

43. The method of claim 41, wherein the restraining step further comprises:
securing a portion of the incus against a bracket mounted within a middle ear cavity.

44. The method of claim 38, wherein the stabilizing step is performed without separating the ossicular chain.

45. The method of claim 37, wherein the receiving step further comprises:
locating the sound reception site of the electromechanical device externally of the skull.

46. The method of claim 37, wherein the receiving step further comprises:
locating the sound reception site of the electromechanical device within the external auditory canal.

47. The method of claim 37, wherein the receiving step further comprises:
locating the sound reception site of the electromechanical device subdermally adjacent the ear.

48. The method of claim 37, wherein the maintaining step further comprises:
prior to fixing a portion of the incus, cutting the incus to separate the incus into two separate portions that do not contact each other.

49. The method of claim 48, wherein the cutting step is performed with a laser.

50. The method of claim 48, wherein the cutting step is applied to the long process of the incus.

51. The method of claim 50 wherein the cutting step further comprises:
selecting the cutting location on the incus to maintain intact the incudostapedial joint.

52. The method of claim 48 wherein the maintaining step further comprises:

mounting the transducer on the first portion and maintaining a separation distance between the transducer and the second portion to prevent tissue reconnection between the second portion and at least one of the transducer and the first portion.

53. A partially implantable apparatus for improving the hearing of a sensorineural hearing impaired subject without causing feedback through the ossicular chain of the subject, comprising:

an artificial sensing transducer for sensing air conducted signals external to the middle ear;

input and output transducer means adapted for cranial location for mediating mechanical and electrical signals having controlled amplification characteristics, the input and output transducer means having electromechanical linkage means for operatively communicatively coupling the artificial sensing transducer to the inner ear of the subject to transmit signals therebetween; and means for maintaining a portion of the ossicular chain in a fixed position to prevent transmission of feedback sound energy from the inner ear to the artificial sensing transducer through the ossicular chain and the external auditory canal.

54. The apparatus of claim 53 wherein the artificial sensing transducer is configured and arranged for disposition external of the subject's external auditory canal.

55. The apparatus of claim 53 wherein the artificial sensing transducer is configured and arranged for disposition within the subject's auditory canal.

56. The apparatus of claim 53 wherein the transducer is a piezoelectric transducer.

57. The apparatus of claim 53 wherein the transducer is an electromagnetic transducer.

58. The apparatus of claim 53 wherein the electromechanical linkage means further comprises:

a connection assembly adapted to be secured to a portion of the subject's ossicular chain.

59. The apparatus of claim 58 wherein the connection assembly further comprises a bracket.

60. The apparatus of claim 58 wherein the connection assembly further comprises a hanger.

61. The apparatus of claim 58 wherein the connection assembly further comprises a combination mounting bracket and removable portion.

62. The apparatus of claim 53 wherein the fixation means further comprises:

means for maintaining a separation between a first portion of the ossicular chain and a second portion of the ossicular chain to prevent transmission of sound energy from the first portion to the second portion.

63. The apparatus of claim 53 wherein the separation means further includes:

means for restraining one of the first and second portions at a distance from the other of the first and second portions.

* * * * *